United States Patent [19]

Bell et al.

[11] Patent Number: 4,932,871

[45] Date of Patent: Jun. 12, 1990

[54] RAPID METHOD FOR PREPARING CHROMOGENIC ALPHA-AMYLASE SUBSTRATE COMPOUNDS AT HIGH PREPARATIVE YIELDS

[75] Inventors: Douglas Bell, Elkhart; Amy Chu, Granger, both of Ind.

[73] Assignee: Miles Inc., Elkhart, Ind.

[21] Appl. No.: 123,375

[22] Filed: Nov. 20, 1987

[51] Int. Cl.$^5$ .................................... C12P 19/18
[52] U.S. Cl. ................................ 435/97; 435/22; 435/96; 435/810
[58] Field of Search ............... 435/96, 97, 22, 810

[56] References Cited

U.S. PATENT DOCUMENTS

| | | | |
|---|---|---|---|
| 3,694,318 | 9/1972 | Klein | 435/22 |
| 4,169,765 | 10/1979 | Keyes | 435/22 |
| 4,225,672 | 9/1980 | Hall | 435/22 |
| 4,237,221 | 12/1980 | Helmgard | 435/22 |
| 4,505,756 | 3/1985 | Nix | 435/97 |

Primary Examiner—Peter D. Rosenberg
Attorney, Agent, or Firm—Daniel W. Collins

[57] ABSTRACT

A method for preparing chromogenic α-amylase substrate compounds at substantially high preparative yields in a relatively short period of time by the transglucosylation of a chromogenic glucoside compound to a maltooligosaccharide chain. The concentration of the maltooligosaccharide compound is greater than about 3 times the concentration of the chromogenic glucoside compound to result in at least about 50% of the chromogenic glucoside compound being converted to the desired chromogenic α-amylase substrate compound.

28 Claims, 6 Drawing Sheets

RAPID METHOD FOR PREPARING CHROMOGENIC ALPHA-AMYLASE SUBSTRATE COMPOUNDS AT HIGH PREPARATIVE YIELDS

BACKGROUND OF THE INVENTION

The present invention relates to chromogenic enzyme substrate compounds which are useful as optical indicator compounds in analytical test systems. In particular, the present invention relates to chromogenic α-amylase substrate compounds for the detection of α-amylase in a liquid test sample.

α-Amylase is an endoenzyme which hydrolyzes complex carbohydrates, such as starch and glycogen, which are polymers of α-D-glucose units linked through the 1 and 4 carbon atoms located on adjacent glucose residues. Although there are many amylase isoenzymes present in serum and urine, the predominant species are from the pancreas (p-type amylase) and salivary glands (s-type amylase), with the p-type comprising approximately one-half of the total amylase activity. During certain disease states, such as acute pancreatitis and salivary lesions, the level of amylase in serum and urine becomes increasingly elevated. Accordingly, the determination of total amylase activity in serum or urine is particularly useful for the clinical diagnosis of pancreatitis and mumps.

A number of methods have been developed over the years to make such determination, including the measurement of the turbidity or viscosity of an aqueous starch solution or the amount of reducing sugar formed in the reaction [Henry, et al., *Clin. Chem.*, vol. 6, p. 434 (1960) and Ware, et al., *Standard Method of Clinical Chemistry*, Vol. 4, p.15 (1963)], as well as kinetic methods [Barbson, et al., *Clin. Chem.*, Vol. 14, p. 802 (1968), Reinderknecht, et al., *Experientia*, Vol. 23, p. 805 (1967), and Klein, et al., *Anal. Biochem.*, Vol. 31, p. 412 (1960)]. Recently, methods have been developed which employ maltooligosaccharides or glucosides as α-amylase substrates whereby glucose or maltose produced by the action of α-amylase is determined by coupled enzyme systems [Lalegeri, et al., *Clin. Chem.*, Vol. 28, p. 1798 (1982), Hagele, et al., *J. Chromatog.*, Vol. 223, p. 69 (1981), Kaufman, et al., *Clin. Chem.*, Vol. 26, p. 846 (1980) and Pierri, et al., *Methods in Enzymatic Analysis*, Vol. 4, p. 146 (1984)]. However, such assays require the elimination of interferants such as endogenous glucose and maltose present in a test sample before the assay can be conducted.

More recently, chromogenic methods have been developed employing maltooligosaccharides coupled to a soluble dye or chromogen which provides a detectable optical signal when the chromogen is liberated. However, since α-amylase is capable of cleaving only covalent bonds between adjacent glucose units, it is necessary to employ an endoenzyme such as α-glucosidase or β-glucosidase to cleave the bond between the final glucose unit and the chromogen coupled thereto. The liberated form of the chromogen has the desired optical activity which can be measured and correlated to the amount of α-amylase present in a liquid test sample. For example, U.S. Pat. No. 4,544,631 describes a chromogenic amylase assay using p-nitrophenyl-α-D-maltooligosaccharide, with four to seven glucose units, as the substrate. The p-nitrophenyl moiety is covalently bound to the reducing end of the maltooligosaccharide through a α-1,4-hemiacetal linkage whereby when hydrolyzed by amylase and an indicator enzyme, such as α-glucosidase, the rate of formation of yellow nitrophenol is used to quantitate amylase activity.

Typically, such chromogenic substrates for α-amylase are prepared employing cyclodextrin glucanotransferase (CDGT), derived from *Bacillus macerans* (EC 2.4.1.19), according to methods known in the art [French, et al., *J. Am. Chem. Soc.*, Vol 76, p. 2387 (1954), Bender, *Carbohydrate Research*, Vol. 78, pp. 133 and 147 (1980), and Wallenfels, et al., *Carbohydrate Research*, Vol. 61, p.539 (1978)]. Such methods rely upon the known glycosyl-transferring properties of CDGT which involves the transfer of a glucoside compound to a pre-formed polysaccharide chain (e.g., α-cyclodextrin) by CDGT, i.e., transglucosylation, to result in the desired α-amylase substrate compound (e.g., maltoheptaoside). In addition to such transglucosylation property, CDGT is also capable of catalyzing the hydrolysis of long-chain maltooligosaccharides into shorter lengths thereof (e.g., glucose, maltosides, maltotriosides, and the like) which do not serve as substrates for α-amylase. Accordingly, it is therefore necessary to provide reaction conditions which maximize the synthetic activity of CDGT while, at the same time, minimize the hydrolytic activity thereof, in order to provide high yields of α-amylase substrate compounds having the required length of the maltooligosaccharide chain. The prior art methods previously described provide reaction conditions which result in low yields of the desired compound (e.g., maltoheptaoside or derivatives thereof), usually less than 5%, and typically require reaction times of 24 hours or more.

Accordingly, it is an object of the present invention to provide a convenient method for preparing chromogenic α-amylase substrate compounds at high preparative yields within a relatively short period of time.

Further, it is an object of the present invention to provide chromogenic α-amylase substrate compounds which are sensitive to the presence of α-amylase to thereby permit the rapid and accurate determination thereof in an analytical test system.

SUMMARY OF THE INVENTION

According to the present invention, chromogenic α-amylase substrate compounds comprising a chromogenic glucoside compound coupled to a maltooligosaccharide chain can be prepared at substantially high preparative yields in a relatively short period of time. In particular, the present inventors have found that by reacting a chromogenic glucoside compound with a maltooligosaccharide in the presence of cyclodextrin glucanotransferase wherein the molar concentration of the maltooligosaccharide is at least about 3 times greater than the concentration of the glucoside compound, resulting in conversion of at least about 50% of the glucoside compound to the desired chromogenic α-amylase substrate compound. Preferably, the chromogenic glucoside compound is reacted with a maltooligosaccharide comprising from between about 3 and 20 glucose units in the presence of greater than about 50,000 units of cyclodextrin glucanotransferase/liter at between about 40° C. and about 55° C. and at from between about pH 5.0 and pH 7.0, preferably pH 6.0, to result in the desired α-amylase substrate compound in about 4 hours.

DESCRIPTION OF THE PREFERRED EMBODIMENTS

Figure 1:
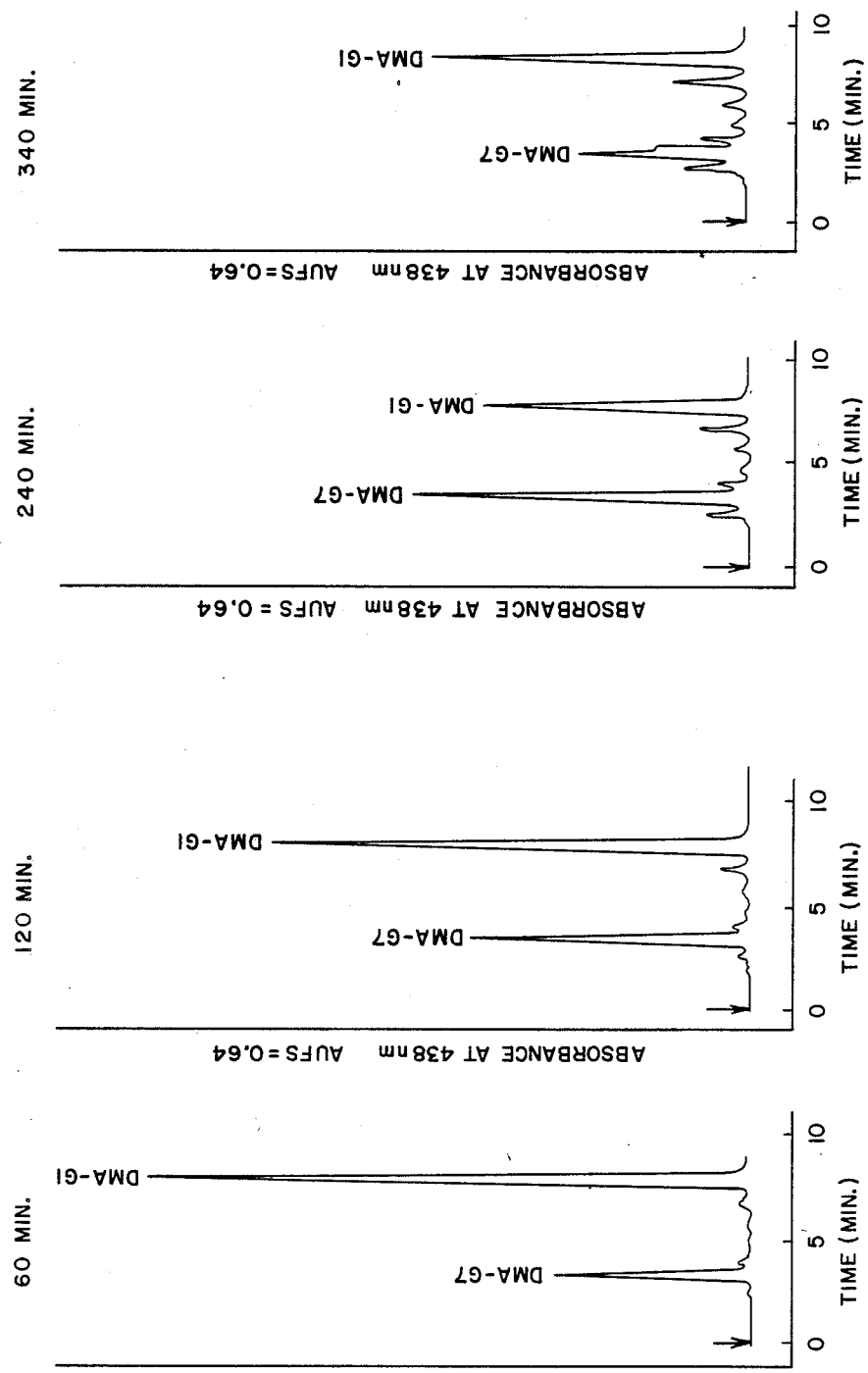
FIG. 1 is a high-pressure liquid chromatography chromatogram profile which demonstrates the amount of a chromogenic α-amylase substrate compound (7-β-maltoheptaosyloxy-9,9-dimethyl-acridin-2-one, i.e., DMA-G7) formed over a period of time relative to a chromogenic glucoside compound (7-β-D-glucopyranosyloxy-9,9-dimethyl-9H-acridin-2-one, i.e, DMA-G1) starting material.

The enzymatic preparation of chromogenic α-amylase substrate compounds according to the present invention is the result of the transglucosylation of a selected chromogenic glucoside compound to a maltooligosaccharide with cyclodextrin glucanotransferase [1,4-α-glucan-4-glucosyltransferase, EC 2.4.1.19] derived from *Bacillus macerans*. Cyclodextrin glucanotransferase, in addition to its hydrolytic and cyclization action, possesses glucosyl transferring activity whereby the chromogenic glucoside compound is enzymatically transferred to a pre-formed maltooligosaccharide chain to form an α-1,4 glucoside linkage between the glucose unit at the reducing end of the maltooligosaccharide chain and the glucose unit at the non-reducing end of the chromogenic glucoside compound.

The hydrolytic action of cyclodextrin glucanotransferase on maltooligosaccharides results in the hydrolysis or break-down of longer maltooligosaccharide chains which can have undesirable effects. For example, where it is desired to transglucosylate a chromogenic glucoside compound to a maltooligosaccharide chain comprising 6 glucose units, cyclodextrin glucanotransferase will not only transfer the desired length maltooligosaccharide to form a linear maltoheptaoside derivative, but it will also hydrolyze maltoheptaosides into shorter chains comprising, for example, 2 or 3 glucose units. Accordingly, the transglucosylation of the chromogenic glucoside compound results in α-amylase substrate compounds having the desired length maltooligosaccharide chain coupled thereto, as well as the undesirable shorter maltooligosaccharide chains coupled thereto which do not provide suitable substrates for α-amylase in a test system for the determination of α-amylase.

According to the present invention, control of the relative concentrations of the chromogenic glucoside compound and the maltooligosaccharide permits the formation of the chromogenic α-amylase substrate compound having the desired maltooligosaccharide chain coupled thereto. In particular, since the concentration of the maltooligosaccharide is at least about 3 times, and preferably about 5 times, greater than the concentration of the chromogenic glucoside compound in carrying out the method of the present invention, the transglucosylation activity of cyclodextrin glucanotransferase is significantly greater than the hydrolytic activity thereof due to the substantially greater presence thereof in the reaction mixture. Accordingly, such transglucosylation activity results in at least about 50% of the glucoside compound present in the reaction mixture being converted to the desired α-amylase substrate compound having the desired length maltooligosaccharide coupled thereto.

It is particularly preferred that the concentration of the maltooligosaccharide be sufficiently in excess over the concentration of the chromogenic glucoside compound to maximize the synthetic activity of cyclodextrin glucanotransferase while, at the same time, minimize the hydrolytic activity thereof. Accordingly, as will be understood by one skilled in the art, such relative concentration can be varied, preferably from between about 3 and 7 times greater, to achieve the maximum synthetic activity and minimum hydrolytic activity of the enzyme.

However, it is also to be understood that the hydrolytic activity of cyclodextrin glucanotransferase nevertheless results in the presence of contaminating species of α-amylase substrate compounds having either undesirably short maltooligosaccharide chains coupled thereto or unsubstituted glucose oligomers. Since such contaminating species would otherwise compete with the desired α-amylase substrate compound when employed in an assay for α-amylase, it is therefore desirable to remove such contaminating species to obtain a substantially pure preparation of the desired α-amylase substrate compound prepared according to the present invention having the desired maltooligosaccharide chain coupled thereto. According to a preferred embodiment of the present invention, such contaminating species are removed by high-pressure liquid chromatography techniques known in the art.

Although the method of the present invention can be carried out from between about 37° C. and 60° C., the activity of cyclodextrin glucanotransferase is significantly less at the lower and upper regions of this range resulting in reaction times of up to, and even greater than, 24 hours. Preferably, the method of the present invention is carried out at from between about 40° C. and about 55° C., more preferably at about 50° C., to result in the aforementioned conversion of the chromogenic glucoside compound to the desired α-amylase substrate compound in significantly less than 24 hours, usually in about 4 hours.

The length of time necessary for preparing the substrate compound according to the present invention further depends upon the concentration of cyclodextrin glucanotransferase in the reaction mixture. In particular, by increasing the concentration of cyclodextrin glucanotransferase from about 33 units/liter to 250 units/liter, the yield of the desired substrate compound increases from between about 14% to 52%, respectively, in about 24 hours. Accordingly, by further increasing the concentration to at least about 50,000 units/liter, preferably 56,000 units/liter, a similar yield of greater than about 50% can be achieved in about 4 hours when carried out at the temperature and relative concentrations of the chromogenic glucoside compound and the maltooligosaccharide as previously described.

The method of the present invention can be carried out employing various chromogenic glucoside compounds known in the art which, when hydrolysed by an appropriate enzyme such as α-glucosidase or β-glucosidase, results in an optically active chromogenic compound, e.g., flourescence, phosphorescence, color, ultraviolet absorbance, and the like, which can be detected and correlated to the amount of α-amylase present in a liquid test sample. Such chromogenic glucoside compounds include, but are not intended to be limited to, phenylglucoside, mononitrophenylglucoside, dinitrophenylglucoside, chloro-nitrophenyl glucoside, indolyl-α-D-glucoside, O-6-deoxy-6-[(2-pyridyl)amine]-α-D-glucoside, umbelliferone, resorufin, and the like. It is to be understood that the present invention can be followed for preparing higher molecular weight saccharides as well as by the transglucosylation of a maltooligosaccharide to, for example, D-glucose, D-glucoheptulose, polygalitol, maltose, maltobionic acid, cellobiose, turanose, sucrose, planteose, melezitose, panose, 6'-(α-D-glucopyranosyl)-maltose, isomaltose and the glucosides α-methyl-D- -glucopyranoside, α-phenyl-D-glucopyranoside, aucubin and phlorizin.

Preferably, the chromogenic glucoside compound is 7-β-D-glucopyranosyloxy-9,9-dimethyl-9H-acridin--2-one (DMA-G1) of the formula:

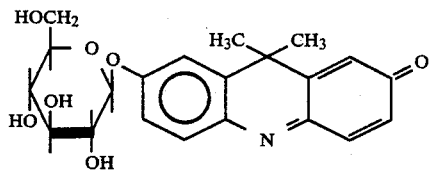

which is prepared according the method described in the copending U.S. application (U.S. Ser. No. 939,855) entitled "Chromogenic Acridinone Enzyme Substrates". According to such method, a 7-hydroxy-9,9-dimethyl-9H-acridin-2-one chromogen, derived from a 7-hydroxy-1,3-dichloro-9,9-dimethyl-9H-acridin-2-one intermediate, is reacted with acetobromoglucose and silver oxide in quinoline to yield 7-(tetra-O-acetyl-β-D-glucopyranosyloxy)-9,9-dimethyl-9H-acridin-2-one. The acetate protecting groups are then hydrolyzed with sodium methoxide in methanol to obtain the desired 7-β-D-glucopyranosyloxy-9,9-dimethyl-9H-acridin-2-one indicator compound for use as the chromogenic glucoside compound herein.

The resulting glucoside has an absorbance ($\lambda_{max}$) of 438 nm (yellow), an extinction coefficient of 27,400, and is soluble in a phosphate buffered solution (pH 7.4). Upon the hydrolysis of the glucoside by β-D-glucosidase from a liquid test sample, the liberated chromogen anion is soluble in the phosphate buffered solution and exhibits an absorbance of 634 nm (blue) to provide a 196 nm change in absorbance maxima. Further, the enzyme cleaves the substrate ($K_{cat}$) at the rate of $1.32 \times 10^4$ mol min.$^{-1}$/mol. active site in a 50 mM phosphate buffered solution (pH 7.4) containing 5.0 mM MgCl$_2$, and exhibits a binding constant ($K_m$) of 0.17 nM. Accordingly, such compound provides a very advantageous substrate for a secondary enzyme, such as β-D-glucosidase, in an assay system for α-amylase.

According to the present invention, the chromogenic glucoside compound is transglucosylated to a maltooligosaccharide comprising from between about 3 and about 20 glucose units as described above. Preferably, the maltooligosaccharide comprises a chain from between about 5 and about 10 glucose units. More preferably, the maltooligosaccharide is a chain comprising 6 glucose units, most preferably in the form of α-cyclodextrin. In particular, during the transglucosylation process as described above, cyclodextrin glucanotransferase enzymatically opens the α-cyclodextrin glucose ring structure to form the desired maltooligosaccharide chain comprising 6 glucose units. The chromogenic glucoside compound is then transglucosylated to the glucoside chain to result in an α-amylase substrate compound comprising the chromogenic glucoside compound coupled to a maltooligosaccharide chain comprising 6 glucose units. Preferably, 7-β-D-glucopyranosyloxy-9,9-dimethyl-9H-acridin-2-one is transglucosylated to α-cyclodextrin to result in greater than about a 50% yield of the desired chromogenic maltoheptaoside, i.e., 7-β-maltoheptaosyloxy-9,9-dimethyl-acridin-2-one (DMA-G7) in about 4 hours. It is to be understood that the amount of DMA-G1 converted to DMA-G7 is significantly less when the reaction is carried out for time periods greater than about or less than about 4 hours. (FIG. 1).

The chromogenic α-amylase substrate compounds prepared according to the present invention are particularly useful in analytical test systems for the determination of α-amylase from a liquid test sample. According to such test systems, α-glucosidase or β-glucosidase is employed as a secondary enzyme, or endoenzyme, whereby α-amylase cleaves the maltooligosaccharide chain into shorter chains thereof to release species of chromogenic maltooligosaccharide compounds such as 7-β-maltosyloxy-9,9-dimethyl-acridin-2-one, 7-β-maltotriosyloxy-9,9-dimethyl-aoridin-2-one and 7-β-maltotetraosyloxy-9,9-dimethyl-acridin-2-one. The α-glucosidase and/or the β-glucosidase present in the test system enzymatically acts upon such chromogenic compounds to liberate an optically active form of the chromogen which can be measured and correlated to the amount of α-amylase present in the liquid test sample.

Typically, such determination is made in a liquid assay environment whereby a liquid test sample containing α-amylase is combined with the α-amylase substrate compound, α-glucosidase and β-glucosidase in an appropriately buffered solution. The change in color of the solution as a result of the liberated chromogen is then measured with, for example, a spectrophotometer, and correlated to the amount of α-amylase present in the liquid test sample.

Alternatively, the aforementioned assay reagents can be incorporated into an analytical test device comprising a carrier matrix such as those known in the art utilized for reagent strips for solution analysis. Preferably, the carrier matrix comprises a bibulous material, such as filter paper, whereby an appropriately buffered solution of the aforementioned assay reagents is employed to impregnate the matrix. Accordingly, the liquid test sample containing α-amylase is applied to such test device and the rate of color change produced by the liberated chromogen is measured with an appropriate instrument and correlated to the amount of α-amylase present in the test sample.

The present invention will now be illustrated, but is not intended to be limited, by the following examples:

EXAMPLE 1

Synthesis of 7-β-D-glucopyranosyloxy-9,9-dimethyl-9H-acridin-2-one (DMA-G1)

(a) Synthesis of 7-Hydroxy-1,3-dichloro-9,9-dimethyl-9H-acridin-2-one.

A mixture of 2-(3'-hydroxyphenyl)-2-propanol (1.52 g; 10.0 mmol) prepared as described by Bruce, et al., *J. Chem. Soc. (C)*, 1627 (1966) and 2,6-dichloroquinone-4-chloroimide (Aldrich Chemical Co., Milwaukee, Wis., USA) (2.10 g; 10.0 mmol) in tetrahydrofuran (5.0 mL) was diluted with $H_2O$ (5.0 mL), chilled in an ice bath and dropwise treated, over 10 min., with aqueous 2.0M NaOH (10.5 mL; 21 mmol). The resulting deep blue reaction mixture was allowed to stir at 0° C. for 1.5 hours and was then blended into a vigorously agitated mixture of saturated aqueous $NH_4Cl$ (500 mL) and ethyl acetate (300 mL). The phases were separated and the aqueous phase was extracted once with ethyl acetate (100 mL), then the combined ethyl acetate layers were washed once with saturated aqueous $NH_4Cl$ (200 mL). The resulting ethyl acetate solution was then washed twice with a solution of $Na_2S_2O_4$ (25 g) in $H_2O$ (250 mL). The combined aqueous washes were extracted once with ethyl acetate (50 mL) then the combined ethyl acetate layers were washed once with saturated aqueous NaCl (brine) (150 mL), dried over $Na_2SO_4$, filtered and freed of solvent in vacuo to obtain a brown tar product. A solution of the brown tar product in methanol (10 mL) was slowly blended into rapidly stirring, deoxygenated (by inert gas purge) aqueous 2.0M HCl (250 mL) at ambient temperature. The resulting suspension was heated in a 100° C. oil bath under an inert gas atmosphere for 1.25 hours during which time a dark, gummy solid separated. The reaction mixture was cooled to ambient temperature, stirred rapidly with ethyl acetate (200 mL) and the phases separated; the aqueous layer was extracted once with ethyl acetate (200 mL) and then the combined ethyl acetate layers were washed once with brine (50 mL). The resulting ethyl acetate solution was oxidized by stirring vigorously for 15 minutes with a solution of $NaIO_4$ (3.0 g) in $H_2O$ (100 mL), then the phases were separated and the ethyl acetate layer was washed once with brine (100 mL), dried over $Na_2SO_4$, filtered and evaporated to dryness in vacuo to obtain a crude form of 7-hydroxy-1,3-dichloro-9,9-dimethyl-9H-acridin-2-one which was then taken up on boiling ethyl alcohol (500 mL) and concentrated by boiling to a volume of ca. 150 mL. Upon cooling, the desired compound separated in the form of fine ruddy-black needles to obtain, after two crops, 2.5 g (82%). A portion of the first crop was recrystallized from ethyl alcohol to obtain an analytical sample having no mp <250° C.

IR(KBr) $cm^{-1}$ 1624, 1492, 1451, 1304, 985, 500; $^1$H NMR (DMSO-$d^6$) δ 1.74 (s, 6H), 6.84 (d of d, $J_1=8.5$ Hz and $J_2=2.4$ Hz, 1H), 7.06 (d, j=2.4 Hz, 1H), 7.50 (d, J=8.5 Hz, 1H), 7.76 (s, 1H); $^{13}$C NMR (DMSO-$d^6$) ppm 172.07, 162.70, 145.73, 141.18, 140.85, 139.23, 134.8, 134.6, 134.28, 132.46, 115.95, 114.12, 26.27 (1 coincident band, one hidden by solvent bands);

Anal. Calcd. for $C_{15}H_{11}Cl_2NO_2$: C, 58.46; H, 3.60; N, 4.55 Found: C, 58.71; H, 3.83; N, 4.34.

(b) Synthesis of 7-Hydroxy-9,9-dimethyl-9H-acridin-2-one.

A solution of the dichloro compound from step.(a) of the present example (2.0 g; 6.49 mmol) in aqueous 1.0M NaOH (60 mL) and ethyl alcohol (40 mL) was treated with Raney Nickel 2800 (W.R. Grace and Co., Baltimore, Md., USA) (1 teaspoon) and hydrogenated at 40 psi $H_2$ with agitation at ca. 70° C. for 5 hours. After cooling to ambient temperature, the reaction mixture was filtered through diatomaceous earth (Celite®, Johns-Manville Corp. Denver, Colo., USA), diluted with $H_2O$ (500 mL) then acidified with aqueous 2.0M HCl (100 mL) and extracted five times with ethyl acetate (200 mL @). The combined ethyl acetate extracts were vigorously stirred with a solution of $NaIO_4$ (4.0 g) in $H_2O$ (300 mL) for 10 minutes at ambient temperature then treated with aqueous 1.0M HCl (100 mL). The phases were separated and the aqueous layer was washed twice with ethyl acetate (50 mL @); the combined ethyl acetate layers were washed once with brine (50 mL), dried over $MgSO_4$, filtered and evaporated to dryness in vacuo. Traces of residual water were removed by azeotroping with toluene and then vacuum drying at 60° C. to obtain the desired dimethyl chromogen (1.38 g; 89%) in the form of a red powder. Recrystallization from ethyl acetate/hexane (1:1) afforded the dimethyl chromogen in the form of ruby-red needles.

(c) Synthesis of 7-(Tetra-O-acetyl-β-D-glucopyranosyloxy)-9,9-dimethyl-9H-acridin-2-one.

A mixture of the dimethyl chromogen from step (b) of the present example (0.2393 g; 1.0 mmol), acetobromoglucose (Sigma Chemical Co., St. Louis, Mo., USA) (0.8224 g; 2.0 mmol) and $Ag_2O$ (0.51 g; 2.2 mmol) was stirred in anhydrous quinoline (7.5 mL) for 17 hours at ambient temperature in a stoppered flask protected from light. The reaction mixture was diluted with ethyl acetate (100 mL), filtered through Celite® and twice extracted with aqueous 1.25M HCL (50 mL @). The combined aqueous extracts were washed once with ethyl acetate (10 mL) then the combined ethyl acetate layers were washed once with brine (20 mL), once with 5.0% aqueous $NaHCO_3$ (50 mL) and once again with brine (20 mL). The ethyl acetate solution was then dried over $Na_2SO_4$, filtered and evaporated to dryness in vacuo to give an orange foam. The foam was crystallized from ethyl acetate/hexane (1:1) to afford 7-(tetra-O-acetyl-β-D-glucopyranosyloxy)-9,9-dimethyl-9H-acridin-2-one (0.498 g; 87%) in the form of golden-yellow tiny needles. A portion was recrystallized as above to obtain an analytical sample having a melting point of 142.0–143.5° C.

IR (KBr) $cm^{-1}$ 2980, 1754, 1637, 1617, 1514, 1368, 1132, 1074, 1038; $^1$H NMR (DMSO-$d^6$) δ 1.52 (s, 6H), 1.91 (s, 3H), 1.99 (s, 3H), 2.01 (s, 3H), 2.02 (s, 3H), 3.98–4.19 (m, 2H), 4.32–4.38 (m, 1H), 5.03–5.13 (m, 2H), 5.42 (t, J=9.6 Hz, 1H), 5.83 (d, J=8.0 Hz, 1H), 6.62 (d of d, $J_1=9.8$ Hz and $J_2=2.1$ Hz, 1H), 6.81 (d, J=2.1 Hz, 1H), 7.04 (d of d, $J_1=8.7$ Hz and $J_2=2.7$ Hz, 1H), 7.27 (d, J=2.7 Hz, 1H), 7.43 (d, J=9.8 Hz, 1H), 7.63 (d, J=8.7 Hz, 1H); $^{13}$C NMR (DMSO-$d^6$) ppm 186.46, 170.00, 169.62, 169.33, 169.12, 158.08, 150.99, 147.31, 141.44, 139.67, 137.32, 133.04, 131.26, 127.47, 115.44, 113.84, 96.15, 72.03, 71.13, 70.58, 68.96, 61.92, 37.13, 32.27, 31.79, 20.52, 20.40, 20.30, (one coincident peak);

Anal. Calcd. for $C_{29}H_{31}NO_{11}$: C, 61.15; H, 5.49; N, 2.46 Found: C, 61.35; H, 5.58; N, 2.24.

(d) Synthesis of
7-β-D-Glucopyranosyloxy-9,9-dimethyl-9H-acidrin-2-one (DMA-G1).

A solution of 7-(tetra-O-acetyl-β-D-glucopyranosyloxy)-9,9-dimethyl-9H-acridin-2-one from step (c) of the present example (0.47 g; 0.82 mmol) in HPLC-grade methanol (30 mL) was cooled in an ice bath, treated with sodium methoxide (20 mg) and allowed to warm to ambient temperature. The hydrolysis reaction was followed by thin layer chromatography (silica gel; methanol/CHCl₃ [15:85]) and was complete in 1.5 hours. The reaction was quenched by addition of acetic acid (ca. 20 μL) and evaporated to dryness in vacuo to give a crude form of the desired glucoside (DMA-G1) as an orange foam. The crude form of the glucoside was chromatographed on silica gel (75 g) using methanol/CHCl₃ (15:85) solvent and the major yellow product band was collected and freed of solvent in vacuo to result in an orange foam that was crystallized from a minimum volume of hot ethanol to obtain the glucoside (0.28 g, 86%) in the form of bright orange tiny needles having a melting point of 232°–233° C. (dec.).

IR (KBr) cm$^{-1}$ 3320, 2900, 1627, 1604, 1500, 1230, 1083; $^1$H NMR (DMSO-d$^6$) δ 1.52 (s, 6H), 3.12–3.19 (m, 1H), 3.23–3.35 (m, 2H), 3.40–3.49 (m, 2H), 3.67–3.72 (m, 1H), 4.59 (t, J=5.2 Hz, 1H), 5.05 (d, J=6.2 Hz, 1H), 5.12 (d, J=4.0 Hz, 1H), 5.35 (d, J=4.4 Hz, 1H), 6.60 (d of d, $J_1$=9.8 Hz and $J_2$=2.1 Hz, 1H), 6.80 (d, J=2.0 Hz, 1H), 7.05 (d of d, $J_1$=8.7 Hz and $J_2$=2.6 Hz, 1H), 7.30 (d, J=2.5 Hz, 1H), 7.43 (d, J=9.8 Hz, 1H), 7.59 (d, J=8.7 Hz, 1H); $^{13}$C NMR (DMSO-d$^6$) ppm 186.15, 159.40, 150.28, 147.40, 141.26, 139.33, 136.65, 132.80, 130.82, 127.00, 115.37, 113.90, 99.90, 77.13, 76.64, 73.16, 69.86, 60.74, 37.00, 31.98, 31.65;

Anal. Calcd. for $C_{21}H_{23}NO_7$: C, 62.83; H, 5.78; N, 3.49 Found: C, 62.49; H, 5.78 N, 3.64.

EXAMPLE 2

Synthesis of
7-β-maltoheptaosyloxy-9,9-Dimethyl-acridin-2-one (DMA-G7).

A reaction mixture of 12.5 mM 7β-D-glucopyranosyloxy-9,9-dimethyl-9H-acridin-2-one (DMA-G1) from step (d) of Example 1, 62.0 mM α-cyclodextrin (Sigma Chemical Co., St. Louis, Mo., USA) and 56 units/mL of cyclodextrin glucanotransferase (EC 2.4.1.19, Ammano Pharmaceutical Co., Japan) in piperazine-N,N'-bis(2-ethanesulfonic acid) buffer (PIPES, pH 6.0) for 4 hours at 50° C. The mixture was then heated at 100° C. (boiling water) for 10 minutes to inactivate the cyclodextrin glucanotransferase, and then evaporated to dryness under a vacuum and redissolved in 0.5 mL water to result in a mixture of the glucoside (DMA-G1), unsubstituted maltooligosaccharides (e.g., glucose, maltose, maltotriose, maltotetrose, maltopentose, maltohexose, maltoheptose, and α-cyclodextrin), and the desired DMA-G7 compound and shorter chain-length chromogenic maltooligosaccharides (7-β-malto,-maltotrio,-maltotetra,-maltopenta and -maltohexaosyloxy-9,9-dimethyl-acridin-2-ones, i.e., hereinafter referred to as DMA-G2, DMA-G3, DMA-G4, DMA-G5 and DMA-G6, respectively) of the formulae shown in Table 1.

Figure 2:
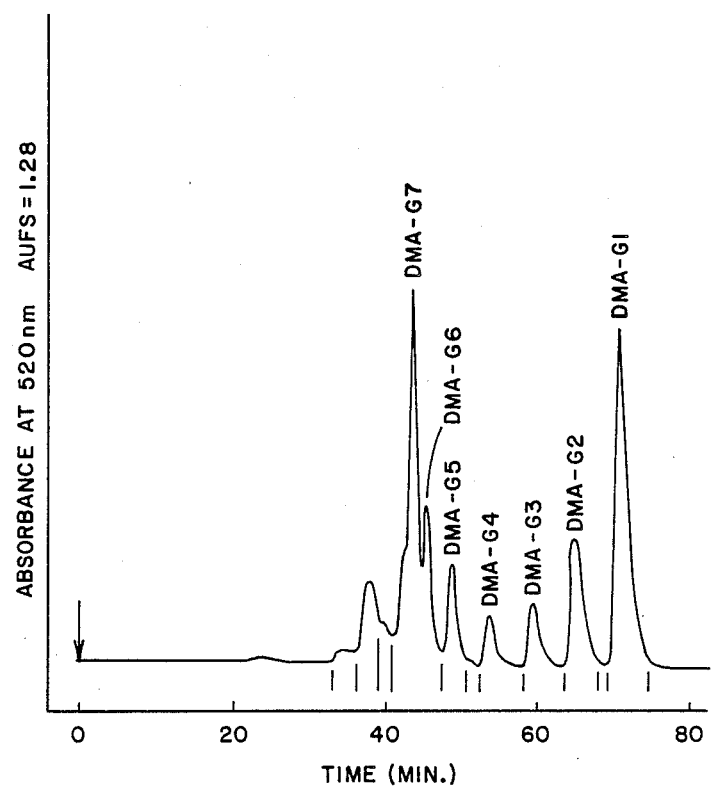
FIG. 2 is a high-pressure liquid chromatography chromatogram which demonstrates the separation of unreacted DMA-G1 from DMA-G7 and shorter chain-length maltooligosaccharide derivatives thereof (DMA-G2 to DMA-G6).
Figure 3:
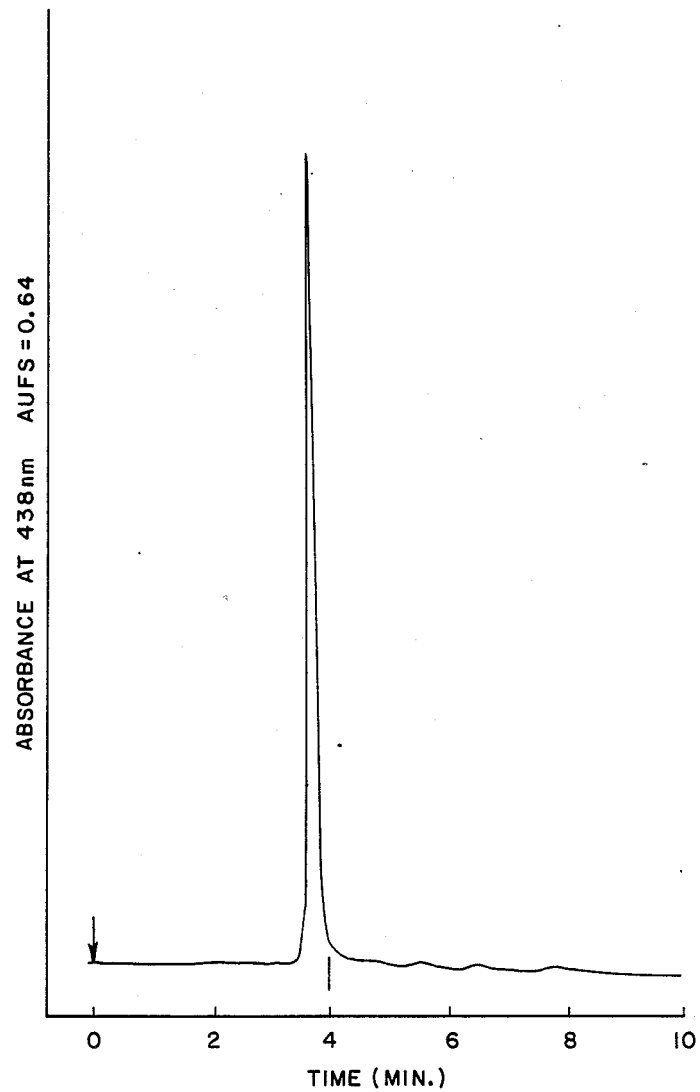
FIG. 3 is a high-pressure liquid chromatography chromatogram which illustrates purified DMA-G7.

The desired DMA-G7 species were separated from DMA-G1 to DMA-G6 species by high pressure liquid chromatography (HPLC) (FIG. 2) employing a preparative reversed-phase C-18 column (Regis Chemical Co., Morton Grove, Ill., USA). The system consisted of two Constametric-III metering pumps, Chromatography Control Module, and a Spectromonitor II detector (all from Laboratory Data Control, Riviera Beach, Fla., USA). The redissolved substrate reaction mixture was injected into the HPLC system and eluted for 90 minutes at a flow rate of 6.0 mL/minute. A linear gradient from 0% to 25% CH₃CN/H₂O was employed for eluting the aforementioned species (DMA-G1 to DMA-G7 and unsubstituted maltooligosaccharides) from the column. The unsubstituted maltooligosaccharides were eluted and removed at the void volume, and the column eluant was monitored at 520 nm to detect the fractions containing the DMA-G1 to DMA-G7 species. The fractions (9.0 mL) containing DMA-G7, DMA-G6, DMA-G5, DMA-G4, DMA-G3, DMA-G2 and DMA-G1 were collected at retention times of 42.5, 44.6, 48.5, 53.1, 58.5, 64.6 and 70.8 minutes, respectively, with a fraction collector (LKB, Bromma, Sweden) whereby about 50% of the DMA-G1 from the reaction mixture was converted to the desired DMA-G7. The fraction containing the DMG7 collected at 42.5 minutes was reanalyzed by HPLC to assure its purity (FIG. 3).

TABLE 1

| n | Reference Symbol |
|---|---|
| 0 | DMA-G2 |
| 1 | DMA-G3 |
| 2 | DMA-G4 |
| 3 | DMA-G5 |
| 4 | DMA-G6 |
| 5 | DMA-G7 |

EXAMPLE 3

Liquid Analytical Test System for the Detection of α-Amylase

Figure 4:
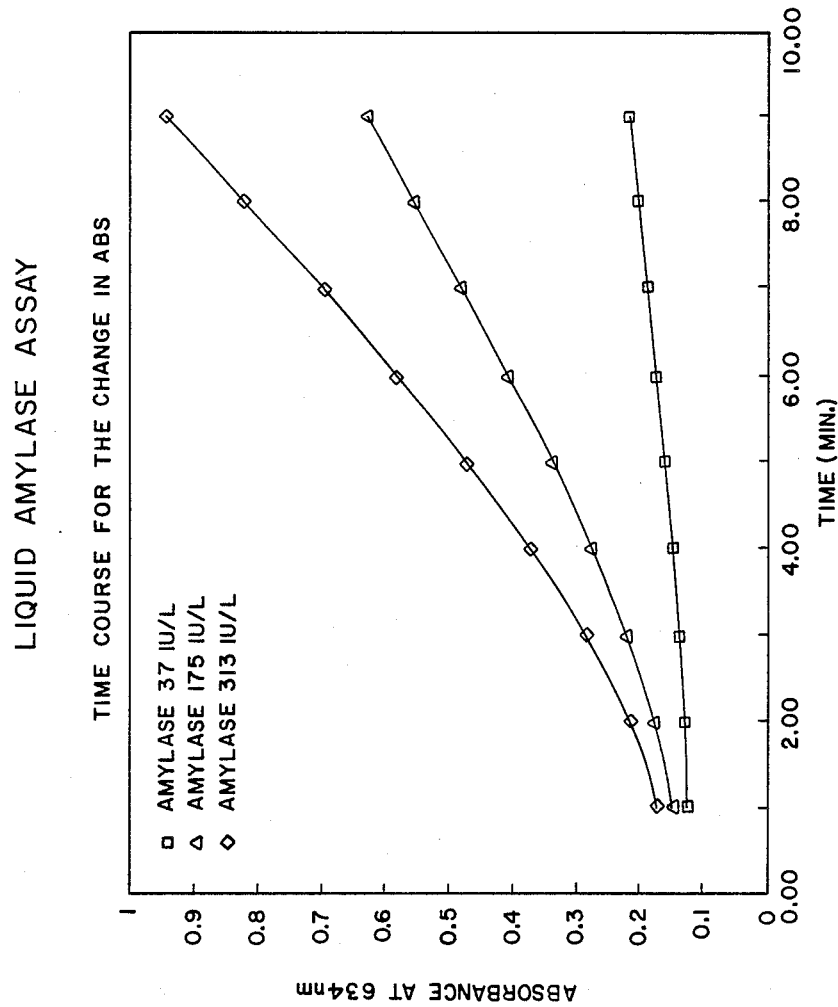
FIG. 4 is a graph which illustrates the time course (rate of color change) of the hydrolysis of DMA-G7 by α-amylase in a liquid test system containing DMA-G7.
Figure 5:
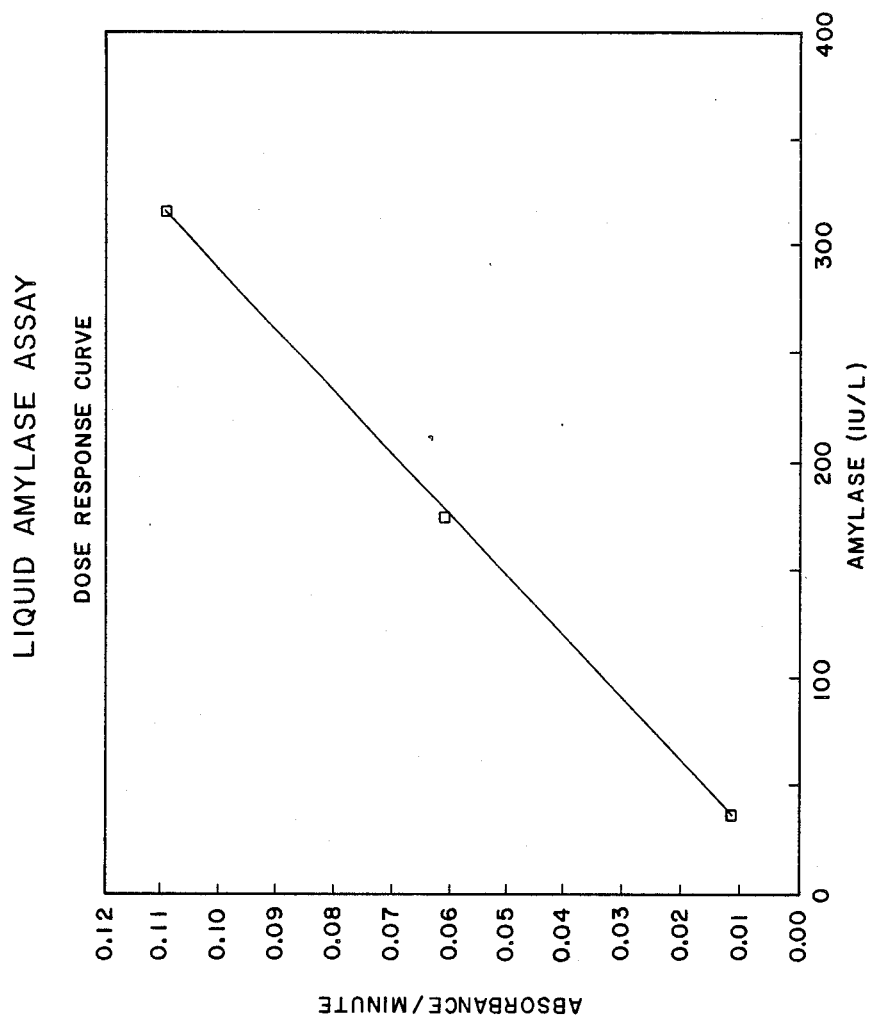
FIG. 5 is a graph which illustrates the dose response to α-amylase of a liquid test system containing DMA-G7.

A liquid α-amylase detection reagent was prepared by combining 1.8 mM DMA-G7 prepared according to Example 2, 38 units of α-glucosidase and 20 units of β-glucosidase in 1.0 mL of buffered solution comprising 50 mM PIPES, 50 mM NaCl, and 5.0 mM calcium chloride (pH 7.0). Amylase control serum (0.025 mL) containing 37 IU/L, 175 IU/L, and 313 IU/L, respectively, of α-amylase were added to the detection reagent, independently, and incubated at 37° C. The enzymatic action of α-amylase on the substrate compound in each of the mixtures liberated the shorter chain chromogenic maltooligosaccharide compounds thereof (e.g., DMA-G2 to DMA-G4) which, in turn, were enzymatically acted upon by the α-glucosidase and β-glucosidase to liberate the optically active form or anion of the 7-hydroxy-9,9-dimethyl- 9H-acridin-2-one chromogen. The rate of color change produced by the liberated chromogen in each of the mixtures was measured at 634 nm on a Cary 219 spectrophotometer (Varian Associates, Inc., Sonnyvale, Calif., USA) from between 1 and 9 minutes after each of the serum samples were added to the detection reagent (Table 2/FIG. 4). The α-amylase reactivities in the samples were calculated by taking an average of three consecutive readings between 3 and 6 minutes and a linear dose response to the α-amylase concentrations was derived therefrom (Table 3/FIG. 5).

TABLE 2

| Time (minutes) | Absorbance (634 nm) | | |
|---|---|---|---|
| | 37 IU/L | 175 IU/L | 313 IU/L |
| 1 | 0.123 | 0.150 | 0.171 |
| 2 | 0.129 | 0.178 | 0.212 |
| 3 | 0.138 | 0.223 | 0.282 |
| 4 | 0.148 | 0.279 | 0.372 |
| 5 | 0.160 | 0.341 | 0.474 |
| 6 | 0.172 | 0.409 | 0.585 |
| 7 | 0.187 | 0.481 | 0.702 |
| 8 | 0.202 | 0.555 | 0.823 |
| 9 | 0.218 | 0.631 | 0.948 |

TABLE 3

| Amylase (IU/L) | Absorbance/Minute |
|---|---|
| 37 | 0.011 |
| 175 | 0.062 |
| 313 | 0.109 |

EXAMPLE 4

Analytical Test Device for the Detection of α-Amylase

A sheet of Whatman 54 filter paper (Whatman, Inc., Clifton, N.J., USA) was immersed into a solution comprising the liquid α-amylase detection reagent prepared according to Example 3, 0.1% Triton X-100 (Sigma Chemical Co., St. Louis, Mo., USA) and 0.5% carboxycellulose, and dried.

Analytical test devices were prepared by mounting 0.5 cm wide ×1.0 cm long segment of the aforementioned impregnated filter paper onto and along the edge of one surface of 0.5 cm×8.125 cm polystyrene supports (Tricite ®, Dow Chemical Co., Midland, Mich., USA) previously laminated with a 2 mm strip of Double Stick ® double-faced adhesive tape (3M Company, St. Paul, Minn., USA).

Figure 6:
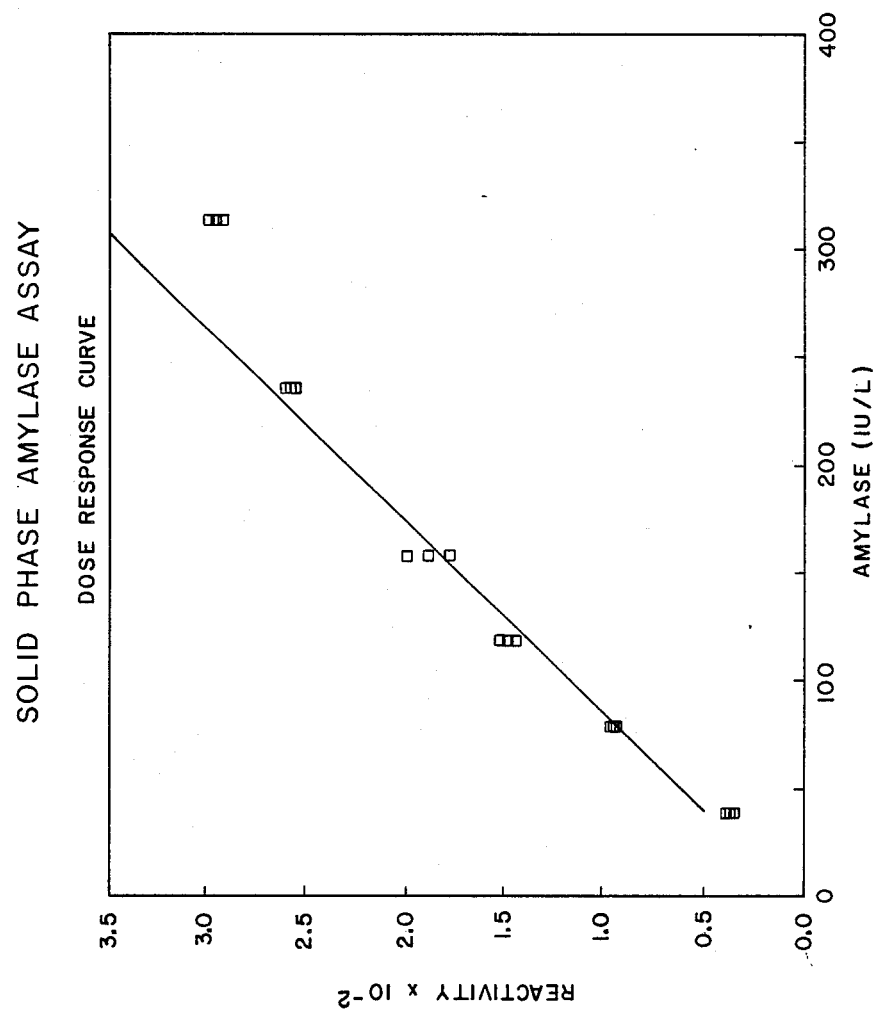
FIG. 6 is a graph which illustrates the dose response to α-amylase of an analytical test device incorporated with DMA-G7.

Three 30 μL aliquots of undiluted serum containing 39 IU/L, 78 IU/L, 117 IU/L, 157 IU/L, 235 IU/L, and 313 IU/L, respectively, of α-amylase were applied, independently, to a test device and the rate of color change produced by the liberated chromogen on each device was measured at 630 nm on a Seralyzer ® reflectance photometer (Miles Inc., Elkhart, Ind., USA) from between 0 seconds and 240 seconds after the serum sample was added to each test device. In order to linearize the reflectance date generated by the rate of color change with respect to the concentration of α-amylase the test device reactivities were determined by taking a linear regression of L(R) where L(R)=a/(R+b) and where R=reflectance, a=0.57986 and b=0.16498, between 180 and 200 seconds, and a linear dose response to α-amylase was derived therefrom (Table 4/FIG. 6).

It will be apparent that many modifications and variations of the invention as herein set forth are possible without departing from the spirit and scope thereof, and that, accordingly, such limitations are imposed only as indicated by the appended claims.

TABLE 4

| Amylase (IU/L) | Reactivity $\times$ $10^{-2}$ |
|---|---|
| 39 | 0.384 |
| | 0.373 |
| | 0.359 |
| 78 | 0.957 |
| | 0.941 |
| | 0.954 |
| 117 | 1.450 |
| | 1.510 |
| | 1.430 |
| 157 | 1.781 |
| | 1.999 |
| | 1.886 |
| 235 | 2.560 |
| | 2.596 |
| | 2.610 |
| 313 | 2.961 |
| | 2.989 |
| | 2.916 |

What is claimed is:

1. A method for preparing a chromogenic α-amylase substrate compound comprising a chromogenic glucoside compound coupled to a maltooligosaccharide chain, said method comprising the steps of:
   (a) reacting said chromogenic glucoside compound with a maltooligosaccharide comprising from between about 3 and about 20 glucose units in the presence of cyclodextrin glucanotransferase wherein the molar concentration of said maltooligosaccharide is at least about 3 times greater than the molar concentration of said chromogenic glucoside compound and said cyclodextrin glucanotransferase is present in at least about 50,000 units/liter.

2. The method of claim 1 wherein the molar concentration of said maltooligosaccharide is less than about 7 times the molar concentration of said chromogenic glucoside compound.

3. The method of claim 2 wherein the concentration of said maltooligosaccharide is at least about 5 times greater than the concentration of said chromogenic glucoside compound.

4. The method of claim 1 wherein said reaction results in a preparation comprising greater than about 50% of said chromogenic α-amylase substrate compound.

5. The method of claim 4 further comprising the step of purifying said chromogenic α-amylase substrate compound by high-pressure liquid chromatography.

6. The method of claim 1 wherein said reaction is carried out at between about 40° C. and about 55° C.

7. The method of claim 1 wherein the concentration of cyclodextrin glucanotransferase is greater than about 50,000 units/liter.

8. The method of claim 1 wherein said maltooligosaccharide comprises 6 glucose units.

9. The method of claim 8 wherein said maltooligosaccharide is α-cyclodextrin.

10. The method of claim 1 wherein said chromogenic glucoside compound is selected from the group consisting of 7-β-D-glucopyranosyloxy-9,9-dimethyl-acridin-2-one, phenylglucoside, mononitrophenylglucoside, dinitrophenylglucoside, chloro- -nitrophenyl glucoside, indolyl-α-D-maltohaptaoside, O-6-deoxy-6--[(2-pyridyl)amine]-α-D-glucoside, umbelliferone, and resorufin.

11. The method of claim 1 wherein said chromogenic glucoside compound is 7-β-D-glucopyrano-syloxy-9,9-dimethyl-acridin-2-one and said maltooligosaccharide is α-cyclodextrin.

12. The method of claim 1 wherein said reaction is carried out for less than about 24 hours.

13. The method of claim 1 wherein said reaction is carried out for about 4 hours.

14. A substantially pure chromogenic α-amylase substrate compound preparation prepared by a process comprising the steps of:
(a) forming a reaction mixture by reacting said chromogenic glucoside compound with a maltooligosaccharide comprising from between about 3 and about 20 glucose units in the presence of cyclodextrin glucanotransferase wherein the molar concentration of said maltooligosaccharide is at least about 3 times greater than the molar concentration of said chromogenic glucoside compound and said cyclodextrin glucanotransferase is present in said reaction mixture in at least about 50,000 units/liter, said reaction mixture comprising said chromogenic glucoside compound coupled to a maltooligosaccharide comprising a predetermined number of glucose units and said chromogenic glucoside compound coupled to a maltooligosaccharide comprising greater than or less than said predetermined number of glucose units;
(b) introducing said reaction mixture into a high-pressure liquid chromatography system wherein said coupled chromogeic glucoside compounds are separated into distinct fractions thereof; and
(c) collecting said distinct fraction containing said chromogenic α-amylase substrate compound coupled to said maltooligosaccharide comprising said predetermined number of glucose units.

15. The preparation of claim 14 wherein said reaction mixture further comprises one or more species of unsubstituted maltooligosaccharides.

16. The preparation of claim 15 wherein said unsubstituted maltooligosaccharides are separated from said chromogenic α-amylase substrate compound by said high-pressure liquid chromatography system.

17. The preparation of claim 14 wherein said reaction mixture comprises greater than about 50% of said chromogenic α-amylase substrate compound.

18. The preparation of claim 14 wherein the molar concentration of said maltooligosaccharide is less than about 7 times the molar concentration of said chromogenic glucoside compound.

19. The preparation of claim 14 wherein the concentration of said maltooligosaccharide is at least about 5 times greater than the concentration of said chromogenic glucoside compound.

20. The preparation of claim 14 wherein said reaction is carried out at between about 40° C. and about 55° C.

21. The preparation of claim 14 wherein the concentration of cyclodextrin glucanotransferase is greater than about 50,000 units/liter.

22. The preparation of claim 14 wherein said maltooligosaccharide comprises 6 glucose units.

23. The preparation of claim 22 wherein said maltooligosaccharide is α-cyclodextrin.

24. The preparation of claim 22 wherein said chromogenic α-amylase substrate compound comprises said chromogenic glucoside compound coupled to 6 glucose units.

25. The preparation of claim 14 wherein said chromogenic glucoside compound is selected from the group consisting of 7-β-D-glucopyranosyloxy-9,9-dimethyl-acridin-2-one, phenylglucoside, mononitrophenylglucoside, dinitrophenylglucoside, chloro-nitrophenyl glucoside, indolyl-α-D-maltohaptaoside, O-6-deoxy-6-[(2-pyridyl)amine]-α-D-glucoside, umbelliferone, and resorufin.

26. The preparation of claim 14 wherein said chromogenic glucoside compound is 7-β-D-glucopyranosyloxy-9,9-dimethyl-acridin-2-one and said maltooligosaccharide is α-cyclodextrin.

27. The preparation of claim 14 wherein said reaction is carried out for less than about 24 hours.

28. The preparation of claim 14 wherein said reaction is carried out for about 4 hours.

* * * * *